United States Patent
Buchanan et al.

(10) Patent No.: US 9,845,272 B2
(45) Date of Patent: *Dec. 19, 2017

(54) HYDROCARBON CONVERSION

(71) Applicant: ExxonMobil Chemical Patents Inc., Baytown, TX (US)

(72) Inventors: John S. Buchanan, Flemington, NJ (US); Samia Ilias, Somerville, NJ (US); Mayank Shekhar, Houston, TX (US); Paul F. Keusenkothen, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/240,651

(22) Filed: Aug. 18, 2016

(65) Prior Publication Data

US 2017/0088487 A1 Mar. 30, 2017

Related U.S. Application Data

(60) Provisional application No. 62/232,909, filed on Sep. 25, 2015, provisional application No. 62/248,374, filed on Oct. 30, 2015.

(30) Foreign Application Priority Data

Nov. 19, 2015 (EP) .................................... 15195311
Dec. 3, 2015 (EP) .................................... 15197702

(51) Int. Cl.
*C07C 2/76* (2006.01)

(52) U.S. Cl.
CPC ............ *C07C 2/76* (2013.01); *C07C 2529/06* (2013.01)

(58) Field of Classification Search
None
See application file for complete search history.

(56) References Cited

U.S. PATENT DOCUMENTS

| | | |
|---|---|---|
| 3,702,886 A | 11/1972 | Argauer et al. |
| 3,702,979 A | 11/1972 | Fletcher et al. |
| 3,832,449 A | 8/1974 | Rosinski et al. |
| 3,960,978 A | 6/1976 | Givens et al. |
| 4,016,218 A | 4/1977 | Haag et al. |
| 4,016,245 A | 4/1977 | Plank et al. |
| 4,021,502 A | 5/1977 | Plank et al. |
| 4,076,842 A | 2/1978 | Plank et al. |
| RE29,948 E | 3/1979 | Dwyer et al. |
| 4,150,062 A | 4/1979 | Garwood et al. |
| 4,227,992 A | 10/1980 | Garwood et al. |

(Continued)

FOREIGN PATENT DOCUMENTS

| | | |
|---|---|---|
| EP | 0293032 | 11/1988 |
| WO | 97/17290 | 5/1997 |

(Continued)

*Primary Examiner* — Tam M Nguyen (57) ABSTRACT

The invention relates to the conversion of light hydrocarbon to higher-value hydrocarbon, such as aromatic hydrocarbon, to equipment and materials useful in such conversion, and to the use of such conversion for, e.g., natural gas upgrading. The conversion can be carried out in two stages, with each stage containing a dehydrocyclization catalyst comprising at least one dehydrogenation component and at least one molecular sieve.

25 Claims, 2 Drawing Sheets

(56) References Cited

U.S. PATENT DOCUMENTS

| | | | |
|---|---|---|---|
| 4,229,424 A | 10/1980 | Kokotailo | |
| 4,234,231 A | 11/1980 | Yan | |
| 4,439,409 A | 3/1984 | Puppe et al. | |
| 4,456,781 A | 6/1984 | Marsh et al. | |
| 4,556,477 A | 12/1985 | Dwyer | |
| 4,826,667 A | 5/1989 | Zones et al. | |
| 4,855,522 A | 8/1989 | Diaz | |
| 4,954,325 A | 9/1990 | Rubin et al. | |
| 5,026,937 A | 6/1991 | Bricker | |
| 5,236,575 A | 8/1993 | Bennett et al. | |
| 5,250,277 A | 10/1993 | Kresge et al. | |
| 5,362,697 A | 11/1994 | Fung et al. | |
| 5,633,417 A | 5/1997 | Beck et al. | |
| 5,675,047 A | 10/1997 | Beck et al. | |
| 6,077,498 A | 6/2000 | Diaz Cabanas et al. | |
| 7,186,871 B2 | 3/2007 | Mitchell et al. | |
| 7,186,872 B2 * | 3/2007 | Juttu | B01J 29/87 585/418 |
| 7,728,186 B2 * | 6/2010 | Iaccino | C07C 2/76 585/407 |
| 8,692,043 B2 | 4/2014 | Lauritzen et al. | |
| 8,835,706 B2 * | 9/2014 | Iyer | C07C 2/76 585/301 |
| 9,732,013 B2 * | 8/2017 | Buchanan | C07C 1/20 |
| 2008/0249342 A1 * | 10/2008 | Iaccino | B01J 29/48 585/402 |
| 2009/0209794 A1 | 8/2009 | Lauritzen et al. | |
| 2015/0065769 A1 | 3/2015 | Henao et al. | |
| 2016/0122256 A1 * | 5/2016 | Wang | C07C 4/18 585/315 |
| 2016/0237002 A1 * | 8/2016 | Vestre | B01J 19/2475 |
| 2017/0007992 A1 * | 1/2017 | Lishchiner | B01J 29/061 |
| 2017/0088486 A1 * | 3/2017 | Buchanan | C07C 2/76 |
| 2017/0088490 A1 * | 3/2017 | Chen | C07C 5/3335 |
| 2017/0088492 A1 * | 3/2017 | Keusenkothen | C07C 5/415 |

FOREIGN PATENT DOCUMENTS

| | | |
|---|---|---|
| WO | 2010/140005 | 12/2010 |
| WO | 2012/078511 | 6/2012 |

* cited by examiner

HYDROCARBON CONVERSION

CROSS-REFERENCE TO RELATED APPLICATIONS

This invention claims priority to and the benefit of U.S. Patent Application Ser. No. 62/232,609 filed Sep. 25, 2015, U.S. Patent Application Ser. No. 62/248,374 filed Oct. 30, 2015, European Patent Application No. 15195311.4 filed Nov. 19, 2015, European Patent Application No. 15197702.2 filed Dec. 3, 2015, all of which are incorporated by reference in their entireties. The following related cases are also incorporated by reference in their entireties: U.S. Patent Application Ser. No. 62/234,240; European Patent Application No. 15197698.2; U.S. Patent Application Ser. No. 62/247,795; European Patent Application No. 15197700.6; U.S. Patent Application Ser. No. 62/234,262; European Patent Application No. 15195314.8; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1; U.S. Patent Application Ser. No. 62/299,730; European Patent Application No. 16167395.9; U.S. Patent Application Ser. No. 62/313,288; European Patent Application No. 16173587.3; U.S. Patent Application Ser. No. 62/313,306, and European Patent Application No. 16173980.0.

FIELD

The invention relates to the conversion of light hydrocarbon to higher-value hydrocarbon such as aromatic hydrocarbon, to equipment and materials useful in such conversion, and to the use of such conversion for, e.g., natural gas upgrading.

BACKGROUND

Aromatic hydrocarbon compounds such as benzene, toluene, and xylenes ("BTX") are frequently used for producing transportation fuels and petrochemicals such as styrene, phenol, nylon and polyurethanes and many others. Processes have been developed for producing light aromatic hydrocarbon from relatively inexpensive feeds, e.g., from paraffinic $C_{4-}$ feeds. The processes typically are carried out using a catalyst comprising molecular sieve, such as ZSM-5 and at least one dehydrogenation metal. These conventional processes typically operate at high temperature and low pressure, which can lead to excessive catalyst coking. Catalyst coking generally worsens under conditions which increase feed conversion, leading to additional operating difficulties.

Processes have been developed for converting less-refractory paraffinic hydrocarbon to aromatic hydrocarbon with decreased selectivity for catalyst coke. For example, U.S. Pat. No. 4,855,522 discloses converting $C_2$, $C_3$, and $C_4$ hydrocarbon with increased selectivity for aromatic hydrocarbon and decreased selectivity for catalyst coke. The process utilizes a dehydrocyclization catalyst comprising (a) an aluminosilicate having a silica:alumina molar ratio of at least 5 and (b) a compound of (i) Ga and (ii) at least one rare earth metal. The reference discloses carrying out the aromatization conversion at a space velocity (LHSV) in the range of from 0.5 to 8 $hr^{-1}$, a temperature ≥450° C. (e.g., 475° C. to 650° C.), a pressure of from 1 bar to 20 bar, and a feed contact time of 1 to 50 seconds.

More recently, catalysts have been developed to further reduce the amount of catalyst coking during the dehydrocyclization of $C_{4-}$ paraffinic hydrocarbon. For example, U.S. Pat. No. 7,186,871 discloses increasing the catalyst's dehydrogenation metal loading to lessen the amount of catalyst coking. It has been found, however, that doing so increases the catalyst's hydrogenolysis activity, resulting in an increase in the amount of methane and other light saturated hydrocarbon in the reaction product and a decrease in the amount of the desired aromatic hydrocarbon. This effect can be mitigated by further increasing catalyst complexity, e.g., by adding an attenuating metal to the catalyst as disclosed in U.S. Pat. No. 8,692,043.

Hydrogenolysis side-reactions can also be mitigated by carrying out the aromatization in two stages. For example, U.S. Pat. No. 8,835,706 discloses aromatization of an ethane-propane feed. The feed, which is obtained from natural gas by cryogenically separating methane, is reacted in a first stage operated under conditions which maximize the conversion of propane to aromatics. In one embodiment, ethane is separated from the first stage's reaction product. The separated ethane is reacted in the second stage to produce aromatics. In another embodiment, aromatics are separated from the first stage's reaction product. In both embodiments, ethane is reacted in the second stage to produce aromatics. The second stage is operated under conditions which maximize the conversion of ethane to aromatic hydrocarbon. The process can be operated continuously by cycling between first and second reactors located in each stage. The first reactor carries out aromatization (reaction mode) while the second reactor undergoes decoking (regeneration mode), and vice versa. The patent discloses that increased catalyst coking can be overcome by utilizing fluidized catalyst beds in the reaction stages. Decreasing the amount of time (the "cycle time") that a fixed bed reactor is operated in reaction mode before switching to regeneration mode can also be used to lessen the amount of coke accumulation.

Improved processes are needed for dehydrocyclization of light paraffinic hydrocarbon that exhibit one or more of a greater feed conversion, a greater yield of aromatic hydrocarbon, and a lesser yield of undesired byproducts such as catalyst coke and $C_{4-}$ hydrocarbon. Processes are particularly desired which can be carried out with catalysts of lesser complexity, in fixed catalyst beds with increased cycle time, and/or with a decreased need for light gas separation.

SUMMARY

Conventional two-stage dehydrocyclization processes carry out at least one separation between the first and second dehydrocyclization stages, e.g., to separate from the first stage product one or more of molecular hydrogen, aromatic hydrocarbon, non-aromatic hydrocarbon other than ethane, etc. The invention is based in part on the development of a process having less or substantially no need for such first product separations. Surprisingly, it has been found that aromatics in the first product are resistant to further reaction in the second dehydrocyclization stage, e.g., resistant to reactions which were expected to convert aromatics in the first product to catalyst coke. Even when the entirety of the first stage product is subjected to dehydrocyclization in the second stage, operating the first stage at a lesser temperature and typically a greater pressure than the second stage, the process as a whole has been found to have a greater selectivity to the desired aromatic hydrocarbon and a lesser selectivity to catalyst coke.

Accordingly, certain aspects of the invention relate to a processes for producing aromatic hydrocarbon from non-aromatic hydrocarbon, e.g., those contained in a feed which comprises ≥1 wt. % of non-aromatic hydrocarbon. The process comprises reacting the feed with a first catalyst under first catalytic dehydrocyclization conditions, which include a temperature $T_1$ in the range of from 400° C. to 630° C., to produce a first product comprising ≥1 wt. % aromatic hydrocarbon. The first catalyst comprises ≥10 wt. % of a first molecular sieve component and ≥0.005 wt. % of a first dehydrogenation component. The process further comprises reacting ≥50 wt. % of the first product, including ≥50 wt. % of the first product's aromatic hydrocarbon, with a second catalyst under second catalytic dehydrocyclization conditions to produce a second product comprising ≥1 wt. % of additional aromatic hydrocarbon. The second catalytic dehydrocyclization conditions include a temperature $T_2$ in the range of from 450° C. to 700° C., wherein $T_1 \leq 0.9 \cdot T_2$. The second catalyst comprises ≥10 wt. % of a second molecular sieve component and ≥0.005 wt. % of a second dehydrogenation component.

Other aspects of the invention relate to systems, apparatus, and catalysts for carrying out the processes of any of the foregoing aspects.

DETAILED DESCRIPTION

Certain aspects of the invention relate to a hydrocarbon conversion process. The feed to the process comprises substantially non-aromatic hydrocarbon. The process includes dehydrocyclization of at least a portion of the feed's non-aromatic hydrocarbon in a first stage to produce a product comprising aromatic hydrocarbon. At least a portion of the first product, e.g., substantially the entire first product or a portion divided from the first product with little or no compositional adjustment, is reacted in a second stage in the presence of a second catalyst under dehydrocyclization conditions to produce a second product comprising additional aromatic hydrocarbon and additional molecular hydrogen. The first stage is operated at a lesser temperature and typically a greater pressure than is the second stage. The invention is based in part on the discovery that the presence of the first product's aromatic hydrocarbon and methane in the second stage is less detrimental to additional aromatic hydrocarbon production than was expected from the teachings of the prior art. Accordingly, the process exhibits (i) an increased conversion of the first product to additional aromatic hydrocarbon, (ii) a greater than expected selectivity for the desired aromatic hydrocarbon, and (iii) a less than the expected selectivity for catalyst coke, even though the second stage is operated at a higher temperature than the first stage. Advantageously, more aromatic hydrocarbon is produced at greater run lengths without catalyst regeneration (e.g., greater cycle time) compared with conventional processes converting substantially the same feed. Unexpectedly, the process has also been found to be less selective for undesirable light hydrocarbon byproducts compared to conventional processes. Even though it is operated at a lesser temperature, some $C_2$ hydrocarbon is produced in the first stage, e.g., by hydrogenolysis of $C_3$ and $C_4$ hydrocarbon that may be present in the feed.

In aspects where the presence of the molecular hydrogen resulting from dehydrogenation might limit aromatic hydrocarbon production in the first stage, it has been found that molecular hydrogen combustion can lessen this effect. Doing so results in a first product comprising little or no molecular hydrogen. Similarly, it has been found that molecular hydrogen combustion can be used in aspects where molecular hydrogen might limit additional aromatic hydrocarbon production in the second stage.

It has also been found that the process is advantageous irrespective of the feed's $C_2$ hydrocarbon content. For example, reacting a light hydrocarbon feeds containing <1 wt. % ethane in the first stage under the specified conditions results in conversion of at least a portion of the feed to ethane. This in turn typically leads to the presence of ethane in the first product. The second stage uses a greater reaction temperature than does the first stage, resulting in the selective conversion of at least a portion of the first product's ethane to additional aromatic hydrocarbon. When the feed contains 1 wt. % to 100 wt. % ethane, utilizing the specified conditions in stages 1 and 2 has been found to increase feed ethane selectivity to aromatic hydrocarbon and decrease feed ethane selectivity to catalyst coke.

DEFINITIONS

For the purpose of this specification and appended claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, including mixtures of hydrocarbon compounds (saturated and/or unsaturated) having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and aromatic hydrocarbon mean hydrocarbon compounds containing at least one aromatic core.

The term "Periodic Table" means the Periodic Chart of the Elements, as it appears on the inside cover of The Merck Index, Twelfth Edition, Merck & Co., Inc., 1996.

The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., selective oxidation) can be the same as or different from the second reaction.

"Dehydrocyclization" means removing hydrogen from and cyclizing a non-cyclic hydrocarbon to produce, e.g., one or more of cyclo-paraffin, cyclo-olefin, and aromatic hydrocarbon. The reaction can be carried out in one or more of (i) one step, which includes both dehydrogenation and cyclization; (ii) two steps, e.g., dehydrogenation followed by cyclization of the dehydrogenated intermediate; and (iii) three or more steps, e.g., normal paraffin dehydrogenation, cyclization of the olefinic intermediate, and additional dehydrogenation (aromatization) of the cyclo-olefin intermediate. The dehydrocyclization (including any dehydrogenation carried out in connection with dehydrocyclization) is "non-oxidative" meaning that the reaction is carried out with little if any oxidative coupling of feed hydrocarbon, intermediate hydrocarbon (if any), or dehydrocyclization product.

The term "selectivity" refers to the production (on a weight basis) of a specified compound in a catalytic reaction. As an example, the phrase "a light hydrocarbon conversion reaction has a 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

The invention includes reacting a feed comprising non-aromatic hydrocarbon in a first stage to selectively convert at least a portion of the non-aromatic hydrocarbon to aromatic hydrocarbon. Representative feeds to the first stage will now be described in more detail. The invention is not limited to these feeds, and this description is not meant to foreclose other feeds within the broader scope of the invention.

Feeds

The feed typically comprises one or more $C_2$ to $C_9$ non-aromatic hydrocarbon compounds, e.g., one or more light hydrocarbon (i.e., $C_2$ to $C_5$) compounds, such as one or more paraffinic light hydrocarbon compounds. For example, the feed can comprise ≥1 wt. % based on the weight of the feed of one or more of (i) paraffinic $C_2$ to $C_9$ hydrocarbon, (ii) aliphatic $C_2$ to $C_9$ hydrocarbon, (iii) aliphatic paraffinic $C_2$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified dehydrocyclization catalyst, e.g., methane, molecular nitrogen, and inert atomic gasses such as argon.

The feed typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feed can contain $C_{5+}$ hydrocarbon, the amount of $C_{5+}$ hydrocarbon when present is typically small, e.g., ≤20 wt. %, such as ≤10 wt. %, or ≤01 wt. %. Typically, the feed contains ≤10 wt. % of $C_{6+}$ saturated hydrocarbon, e.g., ≤5 wt. %.

The feed can contain methane, e.g., ≥1 wt. % methane, such as ≥10 wt. %, or ≥20 wt. %, or ≥60 wt. %. Even though methane is a diluent, i.e., it typically does not react to produce aromatic hydrocarbon or catalyst coke in the presence of the specified dehydrocyclization catalyst under the specified reaction conditions, its presence is beneficial. It is believed that this benefit results at least in part from a decrease in the partial pressure of the feed's $C_2$-$C_9$ hydrocarbon that is achieved when the feed further comprises methane. Decreasing the partial pressure of the feed's $C_2$-$C_9$ hydrocarbon, particularly the partial pressure of the feed's $C_2$-$C_5$ hydrocarbon, has been found to lessen the amount of catalyst coke formed under the specified dehydrocyclization process conditions. Typically, the feed comprises a total of ≤10 wt. % of impurities such as CO, $CO_2$, $H_2S$, and total mercaptan; e.g., ≤1 wt. %, or ≤0.1 wt. %. Optionally, the feed comprises molecular hydrogen, e.g., ≥1 wt. % molecular hydrogen based on the weight of the feed, such as ≥5 wt. %.

In certain aspects, the feed comprises ethane in an amount $A_{1F}$, where $A_{1F}$ is ≥1 wt. %, based on the weight of the feed. In these aspects, $A_{1F}$ is typically ≥5 wt. %, e.g., ≥10 wt. %, such as in the range of from 10 wt. % to 40 wt. %. Suitable feeds include those containing a major amount of ethane, e.g., $A_{1F}$≥50 wt. % based on the weight of the feed, such as ≥75 wt. %, or ≥90 wt. %, or ≥95 wt. %. One representative feed comprises (i) ≥10 wt. % ethane, such as in the range of from 10 wt. % to 40 wt. %; and further comprises (ii) 1 wt. % to 40 wt. % methane, (iii) 20 wt. % to 50 wt. % propane, and (iv) 20 wt. % to 50 wt. % butanes. In other aspects, $A_{1F}$ is ≤1 wt. %, e.g., ≤0.1 wt. %, or ≤0.1 wt. %.

Optionally, the feed contains unsaturated $C_{2+}$ hydrocarbon, such as $C_2$-$C_5$ unsaturated hydrocarbon. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. The feed can be substantially-free of non-aliphatic hydrocarbon. More particularly, the feed can be substantially-free of olefinic and/or aromatic hydrocarbon, where substantially-free in this context means <1 wt. % based on the weight of the feed, such as ≤0.1 wt. %, or ≤0.01 wt. %, or ≤0.001 wt. %. One representative feed comprises <1 wt. % ethane; ≤1 wt. % of aromatic hydrocarbon; and ≥1 wt. % of $C_{3+}$ paraffinic hydrocarbon, e.g., ≥10 wt. % of a mixture of $C_3$ and $C_4$, such as ≥50 wt. %, or ≥75 wt. %, or in the range of 80 wt. % to 99 wt. %. Another representative feed comprises (i) 10 wt. % to 40 wt. % ethane and ≤1 wt. % of aromatic hydrocarbon; with the feed further comprising (ii) 1 wt. % to 40 wt. % methane, (iii) 20 wt. % to 50 wt. % propane, and (iv) 20 wt. % to 50 wt. % butanes.

The feed's light hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., a portion of the second product. Such recycle, when used, can include, e.g., methane, molecular hydrogen, and $C_{2+}$ hydrocarbon, typically $C_2$ to $C_5$ hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, can result in Associated Gas being stranded at or near the reservoir. This in turn can lead to a need for undesirable natural gas flaring. Moreover, even in locations where pipeline facilities are available, Associated Gas may be excluded from the pipeline because it typically exceeds one or more pipeline specifications, e.g., ≤12 wt. % ethane, ≤5 wt. % propane, ≤2 wt. % butanes, a Wobbe Index of from 49.01 $MJ/sm^3$ to 52.22 $MJ/sm^3$, and a heating value of from 36.07 $MJ/sm^3$ to 41.40 $MJ/sm^3$.

Since methane is not detrimental to the process, and is in at least some aspects beneficial, the invention obviates the need for costly and inefficient cryogenic methane separation facilities, such as one or more conventional cold boxes. Typically, obtaining the feed from the source material (e.g., natural gas, such as raw gas) does not include (i) exposing the feed, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention is therefore particularly advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

The feed is conducted to a first stage, where it is reacted in the presence of at least one first stage catalyst in at least one reaction zone operating under catalytic dehydrocyclization conditions. The reaction converts at least a portion of the feed's non-aromatic hydrocarbon to aromatic hydrocarbon. Certain aspects of the first stage will now be described in more detail. The invention is not limited to these aspects, and this description is not meant to foreclose other aspects of the first stage within the broader scope of the invention.

First Stage

Figure 1:
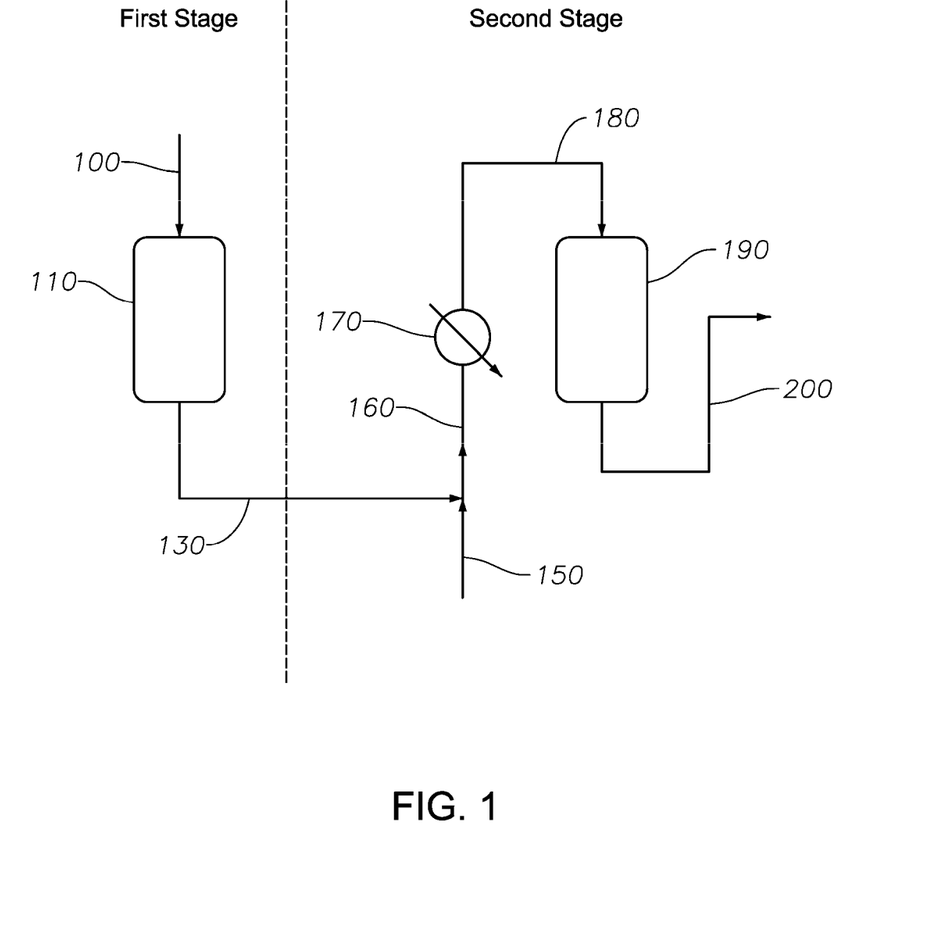
FIG. 1 schematically illustrates certain aspects of the invention which include at least two stages.

Referring to FIG. 1, at least one of the specified feeds 100 is conducted to reaction zone 110, the reaction zone being typically located within a reactor vessel (not shown). The reaction zone includes at least one catalyst having dehydrocyclization functionality for converting at least a portion of the feed's light hydrocarbon to aromatic hydrocarbon and molecular hydrogen. The dehydrocyclization functionality is substantially non-oxidative dehydrocyclization functionality, meaning that the dehydrocyclization catalyst participating in dehydrocyclization reaction in which the production of dehydrogenated, cyclized hydrocarbon occurs predominantly in the absence of forming an oxidized intermediate. The catalyst comprises ≥10 wt. % of a molecular sieve component and ≥0.005 wt. % of a dehydrogenation component.

When the molecular sieve component and dehydrogenation component together comprise less than 100 wt. % of the catalyst, ≥90 wt. % of the remainder of the catalyst can comprise a matrix component, such as ≥99 wt. % of the remainder. Certain aspects of the molecular sieve component, dehydrogenation component, and optional matrix component will now be described in more detail. The invention is not limited to these aspects, and this description is not meant to foreclose other molecular sieve components and/or other dehydrogenation components within the broader scope of the invention.

The catalyst typically comprises the molecular sieve component in an amount ≥20 wt. %, based on the weight of the catalyst, e.g., ≥25 wt. %, such as in the range of from 30 wt. % to 99.9 wt. %. In certain aspects, the molecular sieve component comprises aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically comprises ≥90 wt. % of one or more of the specified molecular sieves, e.g., ≥95 wt. %. In certain aspects, the molecular sieve component comprises at least one zeolite molecular sieve, e.g., ≥90 wt. % zeolite, such as ≥95 wt. %, based on the weight of the molecular sieve component. Although, the molecular sieve component can consist essentially of or even consist of zeolite, in alternative aspects the zeolite(s) is present in the molecular sieve component in combination with other (e.g., non-zeolitic) molecular sieve. The zeolite can be in hydrogen form, e.g., zeolite that has been synthesized in the alkali metal form, but is then converted from the alkali to the hydrogen form. Typically the zeolite is one having a medium pore size and a Constraint Index of 2-12 (as defined in U.S. Pat. No. 4,016,218). Examples of suitable zeolites include ZSM-5, ZSM-11, ZSM-12, ZSM-22, ZSM-23, ZSM-35, ZSM-48, including mixtures and intermediates thereof, such as ZSM-5/ZSM-11 admixture. ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,234,231. Optionally, the zeolite is one comprising at least one set of pores of substantially uniform size extending through the molecular sieve, wherein geometric mean of the cross-sectional dimensions of each of the sets of pores is ≥5 Å, or ≥5.3 Å, e.g., ≥5.4 Å such as ≥5.5 Å, or in the range of 5 Å to 7 Å, or 5.4 Å to 7 Å. ZSM-5 and/or ZSM-12 are suitable, particularly H-ZSM-5. For example, the molecular sieve component can comprise ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 μm, such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

In other aspects, the molecular sieve component comprises at least one molecular sieve of the MCM-22 family, e.g., MCM-22 alone or in combination with other molecular sieve such as one or more of the specified zeolites. As used herein, the term "molecular sieve of the MCM-22 family" (or "material of the MCM-22 family" or "MCM-22 family material" or "MCM-22 family zeolite") includes one or more of:

(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(b) molecular sieves made from a common second degree building block, being a 2-dimensional tiling of such MWW framework topology unit cells, forming a monolayer of one unit cell thickness, preferably one c-unit cell thickness;

(c) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (d) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the molecular sieve component.

When the molecular sieve component comprises at least one aluminosilicate, e.g., at least one zeolite, the aluminosilicate's silica:alumina ratio (substantially the same as the aluminosilicate's $Si:Al_2$ atomic ratio) is typically ≥2, e.g., in the range of from 5 to 100. The silica:alumina ratio is meant to represent the $Si:Al_2$ atomic ratio in the rigid anionic framework of the crystalline aluminosilicate. In other words, aluminum in (i) any matrix or binder or (ii) in cationic or other form within the crystalline aluminosilicate's channels is excluded from the silica:alumina ratio. Alternatively or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

In addition to the molecular sieve component, the catalyst comprises ≥0.005 wt. %, based on the weight of the catalyst, of a dehydrogenation component, e.g., at least one dehydrogenation metal. The dehydrogenation component can comprise one or more neutral metals selected from Groups 3 to 13 of the Periodic Table of the Elements, such as one or more of Ga, In, Zn, Cu, Re, Mo, W, La, Fe, Ag, Pt, and Pd, and/or one or more oxides, sulfides and/or carbides of these metals. Typically, the dehydrogenation component comprises ≥90 wt. % of the one or more of the specified dehydrogenation metals and/or oxide thereof, e.g., ≥95 wt. %, or ≥99 wt. %. For example, the dehydrogenation component can comprise ≥90 wt. % of (A) Ga and/or (B) Zn, including oxides thereof. Typically, the catalyst comprises ≥0.01 wt. % of the dehydrogenation component, based on the weight of the catalyst. For example, the catalyst can comprise ≥0.1 wt. % of the dehydrogenation component, such as ≥0.5 wt. %, or ≥1 wt. %. Those skilled in the art will appreciate that when the dehydrogenation component comprises one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component comprises one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the catalyst in any manner, for example by conventional methods, such as impregnation or ion exchange of the molecular sieve with a solution of a compound of the relevant metal, followed by conversion of the metal compound to the desired form, namely neutral metal, oxide, sulfide and/or carbide. As specified in connection with the molecular sieve component, at least part of the dehydrogenation metal may also be present in the crystalline framework of the molecular sieve. For one representative catalyst, (i) the dehydrogenation component comprises ≥95 wt. % of (A) Ga and/or (B) Zn, and (ii) the first molecular sieve component comprises ≥95 wt. % of H-ZSM-5.

In certain aspects, the dehydrogenation component comprises ≥99 wt. % of one or more of Ga, Zn, and In, and the molecular sieve component comprises ≥99 wt. % of ZSM-5-type zeolite that has been impregnated with the dehydrogenation metal component and/or ion exchanged with the dehydrogenation metal component. For example, the catalyst can comprise Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to acid function of the catalyst and octahedral or non-framework Ga and/or In is believed to contribute to the dehydrogenation function of the catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Besides the molecular sieve component and dehydrogenation component, the catalyst can further comprise an optional matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titanic, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. The catalyst can be in the form of a supported catalyst. Conventional forms of catalyst support can be used, but the invention is not limited thereto.

Alternatively or in addition, the matrix component can include one or more substantially inactive materials. Inactive materials suitably serve as diluents to control the amount of conversion so that products may be obtained economically and in an orderly fashion without employing other means for controlling the rate of reaction. These materials may be incorporated into naturally occurring clays, e.g., bentonite and kaolin, to improve thermal and strength properties (e.g., crush strength) of the catalyst under catalytic conversion conditions. Alternatively or in addition to any phosphorous added to or impregnated into the molecular sieve component, the matrix component can optionally include phosphorous, e.g., to lessen catalyst acidity. Those skilled in the art will appreciate that lessening catalyst acidity decreases the amount of catalyst coke produced during the catalytic conversion of the feed's light hydrocarbon to aromatic hydrocarbon. Suitable phosphorous-containing matrices are disclosed in U.S. Pat. No. 5,026,937, which is incorporated by reference herein in its entirety. The matrix component is optional. In certain aspects, the catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the catalyst's molecular sieve component can comprise ≥95 wt. % of substantially binder free bound molecular sieve, e.g., ≥95 wt. % of substantially binder free ZSM-5, and in particular small crystal H-ZSM-5.

The catalyst can be subjected to one or more treatments, e.g., a selectivation treatment to increase selectivity for producing desired aromatic hydrocarbon compounds, such as paraxylene. For example, the catalyst's molecular sieve component can comprise at least one selectivated molecular sieve. The selectivation can be carried out before introduction of the catalyst into the reactor and/or in-situ in the reactor, e.g., by contacting the catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047, which are incorporated by reference herein in their entirety.

Typically, the catalyst has a surface area as measured by nitrogen physisorption in the range of from 100 m$^2$/g to 600 m$^2$/g, e.g., in the range of from 200 m$^2$/g to 500 m$^2$/g. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

Referring again to FIG. 1, the feed's light hydrocarbon is exposed to a catalytically effective amount of the specified catalyst under catalytic dehydrocyclization conditions in reaction zone 110 that are effective for converting at least a portion of the feed's light hydrocarbon to aromatic hydrocarbon and molecular hydrogen. In certain aspects, the catalytic dehydrocyclization conditions include exposing the feed to a temperature $T_1$ in the range of from 400° C. to 630° C., and a pressure $P_1$ that is sufficient for carrying out the dehydrocyclization. Typically, $T_1$ is in the range of from 450° C. to 605° C. Typically, $P_1$ is ≥20 psia (137.9 kPa) e.g., ≥35 psia (241.3 kPa), such as in the range of from 35 psia (241.3 kPa) to 300 psia (2070 kPa). For example, $P_1$ can be in the range of from 35 psia (241.3 kPa) to 300 psia (2070 kPa), such as 37 psia (255.1 kPa) to 80 psia (522 kPa), or 40 psia (275.8 kPa) to 80 psia (522 kPa), or 45 psia (310.2 kPa) to 80 psia (522 kPa). Generally, the catalytic dehydrocyclization conditions further include a weight hourly space velocity (WHSV) in the range of from 0.1 hr$^{-1}$ to 20 hr$^{-1}$, e.g., 0.2 hr$^{-1}$ to 5 hr$^{-1}$, such as 0.3 hr$^{-1}$- to 1.0 hr$^{-1}$. WHSV is based on the feed's $C_{2+}$ hydrocarbon content, and is the hourly rate of the feed's $C_{2+}$ hydrocarbon (in grams) per gram of catalyst. In a particular aspect, the average temperature across any reaction zone within stage 1 (and across any catalyst bed located within a reaction zone of stage 1) is ≤600° C. Typically, the feed is not exposed to a temperature ≥630° C. at the inlet to reaction zone 110.

Since the dehydrocyclization reaction of stage 1 is carried out at a relatively large pressure (relative to the pressure of stage 2), hydrogen is produced by the dehydrocyclization reaction at a relatively large partial pressure. It was expected that the large partial pressure of hydrogen would suppress feed dehydrogenation, leading to a decrease in the yield of $C_{6+}$ hydrocarbon, such as aromatic hydrocarbon. Surprisingly, this has been found to not be the case: the relatively large hydrogen partial pressure in stage 1 has been found to lessen the rate of catalyst coke accumulation with little or no decrease in the yield of aromatic hydrocarbon. For example, when the dehydrocyclization conditions of the first stage include a pressure $P_1$≥35 psia (241.3 kPa, the dehydrocyclization reaction can be sustained for a time duration ≥50 hours, e.g., ≥100 hours, such as ≥200 hours, or ≥500 hours with a decrease in the yield of $C_{6+}$ hydrocarbon of ≤10%, e.g., ≤5%, such as ≤1%.

Reaction zone 110 contains at least one bed of the specified catalyst. The catalyst can be in particulate form, with the dehydrocyclization reaction taking place as the feed traverses the catalyst bed. The catalyst bed can be one or more of a fixed, moving, or fluidized catalyst bed. In a fixed bed (also called a packed bed), the catalyst remains stationary in the reaction zone. The feed enters the reaction zone proximate to the upstream end of reactor 101. After the dehydrocyclization reaction is carried out in the bed, the first product exits the reaction zone near the downstream end of reactor 110. The reaction zone within the reactor establishes a fixed reference frame, and the catalyst bed is "fixed" in the sense that it is substantially immobile with respect to the fixed reference frame during the dehydrocyclization reaction, e.g., ≥90 wt. % of catalyst associate with a bed is located in substantially fixed positions within the bed. The reactor can be, e.g., an adiabatic single bed, a multi-tube surrounded with heat exchange fluid or an adiabatic multi-bed with internal heat exchange, among others. For example, reaction zones 110 and/or zone 120 can each comprise a plurality (e.g., three) of fixed catalyst beds, optionally with provisions for adding heat to the process (i) at one or more locations between at least two of the beds, and/or (ii) upstream and/or downstream of the reaction zone(s). At least one substantially similar second reaction zone (not shown) can be operated in parallel with reaction zone 110, so that reaction zone 110 can be operated in reaction mode (dehydrocyclization mode) while the second reaction zone is operated in regeneration mode, to regenerate the second reaction zone's catalyst. Continuous or semi-continuous operation can be carried out by alternating reaction and regeneration modes in the reactor 110 and the second reactor. The reaction zones of the first stage (e.g., zone 110 and/or zone 120) are typically operated in reaction mode for an average cycle time ≥50 hours, e.g., ≥75 hours, such as ≥100 hours, or ≥120 hours, at an aromatics yield in each zone that is ≥75% of that attained at the start of dehydrocyclization mode, e.g., ≥90%, such as ≥95%.

In a moving bed, particles of the specified catalyst flow under the influence of an external force such as gravity. The catalyst particles substantially maintain their relative positions to one another during the flow, resulting in a movement of the bed with respect to the fixed reference frame. Average flow of the specified feed with respect to the catalyst flow can be concurrent, countercurrent, or cross-current.

In a fluidized bed, a fluidizing medium (typically in the vapor phase) is conducted through the catalyst bed at a velocity sufficient to suspend the catalyst particles within the bed. The bed suspended catalyst particles typically has the appearance of a boiling fluid. The fluidizing medium's velocity is selected such that the fluidizing medium exerts a sufficient force on the catalyst particles to substantially balance the weight of the catalyst bed.

Conventional fixed, moving, and/or fluidized beds can be used in reaction zone 110 and in optional reaction zone 120, but the invention is not limited thereto. In the reactor beds of stages 1 and 3, the temperature drop across a reactor bed is typically in the range of from 20° C. to 200° C., e.g., in the range of from 50° C. to 150° C.

Since conversion of light hydrocarbon to aromatic hydrocarbon is endothermic, it can be desirable to transfer heat to one or more reaction zones of the first stage. One way to do this is illustrated schematically in FIG. 2, where the first stage includes two reaction zones, 110 and 120. Zones 110 and 120 can be located in the same reactor vessel or in different vessels. As shown, feed 100 is conducted to first reaction zone 110 which contains at least one bed of the specified catalyst. Reaction effluent comprising aromatic hydrocarbon, an unconverted portion of the feed's light hydrocarbon, reaction by-products, etc., is conducted away from first reaction zone 110 via conduit 111 to heat transfer 112. Heat is transferred to the reaction effluent in heat transfer stage 112, and the heated effluent is conducted via conduit 113 to second reaction zone 120. The method for carrying out heat transfer 112 is not critical, provided it is capable of transferring to the first reaction zone's effluent sufficient heat to replace at least a portion of the heat consumed in the endothermic dehydrocyclization reaction of the first reaction zone, so that the desired conversion and selectivity can be achieved in the second reaction zone. For example, heat transfer 112 can include direct and/or indirect heat transfer. Direct heat transfer can be carried out using methods disclosed in U.S. Pat. No. 5,026,937, for example, which include selective combustion of molecular hydrogen in the first reaction zone's effluent. Oxidant for sustaining the selective combustion can be introduced via line 140 and combined with the first stage effluent. The combined stream is conducted via line 141 to heat transfer 112. Typically, sufficient oxidant to combust an amount of the available molecular hydrogen that is appropriate for the desired amount of heat transfer. Generally, at least a portion of the available molecular hydrogen is not combusted. Indirect heat transfer can be carried out using one or more heat exchangers, for example. The heat transfer can include electric heating, which can utilize electric power. For example, electric power can be produced proximate to the process using one or more electric generators. Suitable electric power sources include those which (i) produce electricity by chemical and/or electrochemical conversion and/or (ii) produce electric power from one or more mechanical power sources, e.g., from shaft power. Shaft power can be produced by combusting one or more combustible materials in turbo machinery, for example. Suitable combustible materials, e.g., hydrocarbon, molecular hydrogen, carbon monoxide, etc., can be separated from one or more of the feed's source material, the feed, the first product, and the second product. Besides adding heat, removing molecular hydrogen from the first stage effluent has been found to desirably increase selectivity to aromatic hydrocarbon in the second zone of the first stage and in the second stage.

Figure 2:
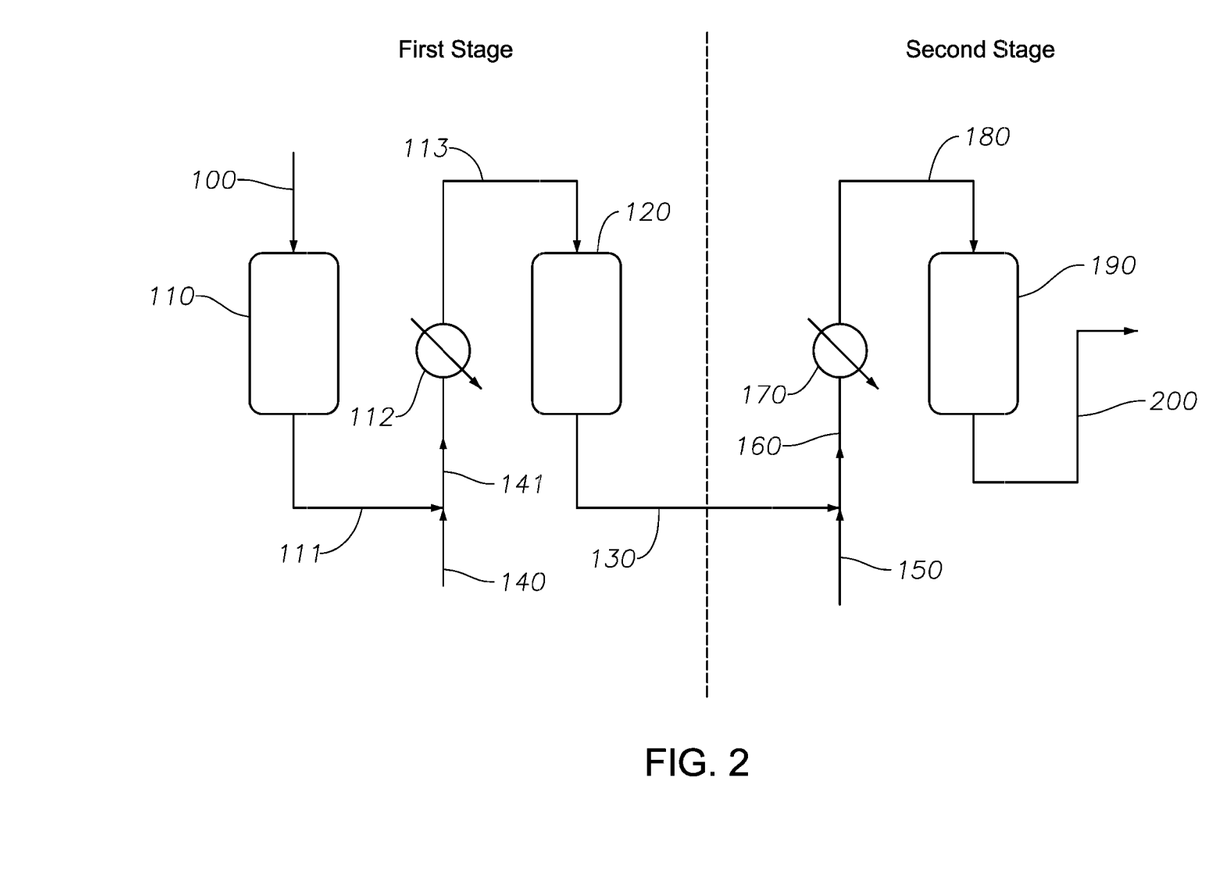
FIG. 2 schematically illustrates certain aspects of the invention in which the first stage includes two reaction zones. Heat is transferred to the first reaction zone's effluent, and the heated effluent is then conducted into the second reaction zone.

Alternatively or in addition, heat can be provided by oxidizing at least a portion of any molecular hydrogen as may be present at other locations in the first stage, e.g., in proximity to dehydrocyclization. For example, oxidant can be introduced into one or more beds of the first catalyst and/or at one or more locations between beds of the first catalyst. The molecular hydrogen combustion can be selective hydrogen combustion, e.g., by including selective hydrogen combustion catalyst with the first dehydrocyclization catalyst and/or at one or more locations between beds of the first dehydrocyclization catalyst. This can be carried out by introducing sufficient oxidant to combust an amount of the available molecular hydrogen that is appropriate for the amount of heating that is desired at the combustion location.

Conventional oxidant can be used for the molecular hydrogen combustion, although the invention is not limited thereto. Suitable oxidant includes, e.g., molecular oxygen, air, and molecular oxygen in air. The combustion can be selective molecular hydrogen combustion, e.g., combustion carried out in the presence of a catalyst having selectivity for combusting molecular hydrogen to produce water over combusting hydrocarbon to produce CO and/or $CO_2$.

The heated effluent is reacted in reaction zone 120 to produce the first product. The first product includes (i) unreacted feed, including unconverted diluent, and (ii) vapor-phase and/or liquid-phase products of the dehydrocyclization reaction and other reaction pathways of the first stage, product phase being that subsisting at the outlet of the downstream-most dehydrocyclization reaction zone of stage 1. Typically, the first product does not include solid (e.g., catalyst coke) and/or semi-solid (e.g., catalyst coke precursors) products of dehydrocyclization and other reaction pathways of the first stage, as these generally remain in the first stage until they are removed during regeneration mode.

The number of catalyst beds, the bed configuration, the dehydrocyclization catalyst, and dehydrocyclization conditions can be the same as or different from those of reaction zone 110, but are typically substantially the same. The first and second reaction zones can be located within the same reaction vessel, but this is not required. As shown in FIGS. 1 and 2, where like index numbers in each figure refer to features performing substantially the same function, the first product is conducted away from the first stage via line 130.

When the feed of line 100 comprises $A_{1F}$ wt. % ethane, wherein $A_{1F} \geq 1$ and the first stage is operated under the specified conditions, the first product comprises (i) ≥1 wt. % aromatic hydrocarbon, (ii) molecular hydrogen, (iii) $A_{1P}$ wt. % ethane, wherein $A_{1P} \geq 0.75 \cdot A_{1F}$, such as $A_{1P} \geq A_{1F}$, or $A_{1P} \geq 1.5^* A_{1F}$, or $A_{1P} \geq 2 \cdot A_{1F}$. The amount of aromatic hydrocarbon can be, e.g., ≥5 wt. %, such as ≥10 wt. %, or in the range of from 1 wt. % to 90 wt. %, or 10 wt. % to 75 wt. %.

When the feed comprises ethane and $C_{3+}$ light hydrocarbon, the catalyst and conditions in reaction zone 110 (and optional reaction zone 120, when present) can be selected from among those specified for the first stage to provide (i) ≤25 wt. % conversion of the feed's ethane, such as ≤10 wt. %, or ≤5 wt. %, or ≤1 wt. % and (ii) ≥25 wt. % conversion of the feed's $C_{3+}$, e.g., ≥50 wt. %, or ≥75 wt. %. Typically, one or more of the catalyst mass, catalyst volume, and feed flow rate are selected to achieve a $C_{3+}$ conversion (weight basis) ≥90%, such as ≥95%, or ≥98%. In certain aspects, $A_{1F} \geq 10$, and the feed further comprises 1 wt. % to 40 wt. % methane; 20 wt. % to 50 wt. % propane; and 20 to 50 wt. % butanes. In these aspects, the first product can comprise ≥10 wt. % aromatic hydrocarbon, $A_{1P}$ wt. % ethane, 1 wt. % to 40 wt. % methane, ≤2 wt. % propane, and ≤1 wt. % butanes. Typically, in these aspects, $A_{1P} \geq A_{1F}$, e.g., $A_{1P} \geq 1.5 \cdot A_{1F}$, such as $A_{1P} \geq 2 \cdot A_{1F}$. The increased ethane content of the first product compared to the feed is believed to result from hydrogenolysis of $C_{3+}$ feed components. Although the first stage dehydrocyclization reaction is selective for aromatic hydrocarbon, (i) ethane conversion products can also include methane and catalyst coke and (ii) $C_{3+}$ conversion products can also include ethane, methane, and catalyst coke. Accordingly, the amount of ethane in the first product can be considerably larger than that of the feed, e.g., stage 1 ethane conversion ("$X_{1E}$") can be less than zero, corresponding to a net production of ethane. For example, in aspects when the feed comprises <1 wt. % ethane, such as ≤0.1 wt. % ethane, ≤1 wt. % of aromatic hydrocarbon, and ≥1 wt. % of $C_{3+}$ paraffinic hydrocarbon, then the first product can comprise ≥10 wt. % aromatic hydrocarbon, molecular hydrogen, $A_{1P}$ wt. % ethane, 1 wt. % to 40 wt. % methane, ≤2 wt. % propane, and ≤1 wt. % butanes, wherein $A_{1P} \geq 1$ wt. %, e.g., ≥5 wt. %, such as ≥10 wt. %.

Those skilled in the art will appreciate that within the ranges of process parameters specified for the first stage dehydrocyclization, there are process conditions which result in a maximum propane conversion to aromatic hydrocarbon "$X_{MP}$". Unlike conventional multi-stage processes, the first stage is typically operated at a propane conversion to aromatic hydrocarbon that is less than $X_{MP}$. Instead, when the feed to the first stage comprises propane and/or when propane is produced in the first stage, process conditions are generally selected so that the initial (start of run) propane conversion to aromatic hydrocarbon in stage one "$X_{1P}$" is ≤0.95·$X_{MP}$. Typically, $X_{1P} \leq 0.90 \cdot X_{MP}$, e.g., ≤0.85·$X_{MP}$, or ≤0.80·$X_{MP}$, or ≤0.75·$X_{MP}$. It has been found that operating stage one under conditions which provide $X_{1P} \geq X_{MP}$ lead to excessive catalyst coking, typically resulting in a shortened cycle time in fixed bed operation. The same effect is observed for conversion of butanes to aromatic hydrocarbon, but with less sensitivity to changes in stage 1 process conditions. Instead of operating at maximum conversion of butanes to aromatic hydrocarbon) $X_{MB}$, the specified process conditions typically result in an initial (start of run) conversion of butenes to aromatic hydrocarbon ("$X_{1B}$") that is less than $X_{MB}$, e.g., $X_{1B} \leq 0.995 \cdot X_{MB}$, such as ≤0.99·$X_{MB}$, or ≤0.985·$X_{MB}$.

Second Stage

Returning to FIGS. 1 and 2, a first product is conducted away from the first stage via line 130. In aspects shown schematically in FIG. 1, the first product comprises ≥90 wt. % of the effluent of reaction zone 110, e.g., ≥95 wt. %, such as ≥99 wt. %. In aspects shown schematically in FIG. 2, the first product comprises ≥90 wt. % of the effluent of reaction zone 120, e.g., ≥95 wt. %, such as ≥99 wt. %. Typically, at least 50 wt. % of the first product is conducted to the second stage, e.g., ≥75 wt. %, such as ≥90 wt. %. Typically, inter-stage compositional separation is not used, although it is within the scope of the invention to (i) remove at least a portion of the first product's methane upstream of the second stage and/or (ii) divide the entirety of first product into two or more streams, with one stream comprising ≥50 wt. % of the entirety of the first product being conducted to the second stage, e.g., ≥75 wt. %, such as ≥90 wt. %, or ≥95 wt. %; and one or more additional streams being conducted away from the process. Typically, the portion of the first product that is reacted under dehydrocyclization conditions in the second stage comprises ≥50 wt. % of the first product's aromatic hydrocarbon, e.g., ≥75 wt. %, such as ≥90 wt. %, or ≥95 wt. %; and ≥50 wt. % of the first product's molecular hydrogen, such as ≥90 wt. %, or ≥95 wt. %. Typically, the portion of the first product that is reacted under dehydrocyclization conditions in the second stage comprises ≥50 wt. % of the first product's ethane, e.g., ≥75 wt. %, such as ≥90 wt. %, or ≥95 wt. %; and ≥50 wt. % of any other (i.e., besides ethane) non-aromatic hydrocarbon in the first product, e.g., ≥75 wt. %, such as ≥90 wt. %, or ≥95 wt. %.

In certain aspects, the process includes a second heat transfer 170 to provide to the first product at least a portion of the heat needed for carrying out the second stage's dehydrocyclization reaction. Any convenient heating method can be used, such as those described in connection with heat transfer 112. Heated first product is conducted to reaction zone 190 for converting at least a portion of the first product's ethane to additional aromatics. When molecular hydrogen combustion, e.g., selective hydrogen combustion, is used to provide direct heating in stage 112, oxidant for supporting the combustion can be introduced via line 150. The oxidant can be the same as that specified for the first stage, but this is not required. Using hydrogen combustion in heat transfer 170 decreases the amount of molecular hydrogen in the first product, although typically ≥50 wt. % of the first product is conducted via line 180 to reaction zone 190, e.g., ≥75 wt. %, such as ≥80 wt. %, or ≥90 wt. %. When heat transfers 112 and/or 170 include direct heat transfer by hydrogen combustion, the feed to stages 120 and/or 180 typically include the products of such combustion, e.g., water. Heat transfers 112 and 170 can be carried out in proximity to a dehydrocyclization reaction zone, e.g., within a reactor vessel containing a dehydrocyclization reaction zone. As in the first stage, certain aspects include as an alternative or in addition to heat transfers 112 and/or 170 molecular hydrogen combustion carried out in proximity to dehydrocyclization. For example, oxidant can be introduced into one or more beds of the second catalyst and/or at one or more locations between beds of the second catalyst. The molecular hydrogen combustion can be selective hydrogen combustion, e.g., by including selective hydrogen combustion catalyst with the second dehydrocyclization catalyst and/or at one or more locations between beds of dehydrocyclization catalyst. Oxidant can be obtained from an external source, e.g., from the same source as is used to supply oxidant to conduits 140 and/or 150.

Those skilled in the art will appreciate that molecular hydrogen combustion, even selective hydrogen combustion, is not perfectly selective, and, consequently a portion of the first product's aromatic hydrocarbon and non-aromatic hydrocarbon will be combusted also. Typically, the amount of total hydrocarbon combustion is ≤10 wt. %, e.g., ≤5 wt. %, such as ≤1 wt. %, based on the total amount of hydrocarbon in that portion of the first product subjected to selective hydrogen combustion in heat transfer 170. This effect can be overcome by increasing the amount of the first product conducted to the second stage, e.g., an amount ≥55 wt. % of the first product, such as ≥60 wt. %, in order to contact with the specified second catalyst ≥50 wt. % of the first product, including ≥50 wt. % of the first product's aromatic hydrocarbon.

Certain aspects include separating conducting away a portion of the first product's methane from the process upstream of the second stage. This can be desirable when the first product would otherwise contain more methane than is needed for lessening the ethane partial pressure in stage 2 into a desirable range. In these aspects, the total amount of first product transferred to the second stage is increased, in order to contact with the specified second catalyst ≥50 wt. % of the first product, including ≥50 wt. % of the first product's aromatic hydrocarbon. Typically, however, there is substantially no compositional adjustment of the first product upstream of the second stage, and ≥50 wt. % of the entirety of the first product is conducted to the second stage, e.g., ≥75 wt. %, such as ≥90 wt. %.

Referring again to FIGS. 1 and 2, the second stage includes conducting the heated first product (or portion thereof) away from stage 170 via conduit 180 to reaction zone 190 for carrying out additional catalytic dehydrocyclization in the presence of a second dehydrocyclization catalyst. The feed to reaction zone 190 contains $A_{2F}$ wt. % ethane. Typically, $A_{2F}$ is ≥0.1, e.g., ≥1, such as ≥5, or ≥10. A second product 200 comprising additional aromatic hydrocarbon (additional to those of the first product) is conducted away from reaction zone 190. If desired, at least a portion of the second product's aromatic hydrocarbon can be separated and conducted away, i.e., for storage and/or further processing.

Reaction zone 190 includes at least one bed of the second dehydrocyclization catalyst. The catalyst bed can be located in a reactor vessel, which can be the same vessel as is used for reactor zone 110, the same vessel as is used for zone 120 (in aspects having zone 120), or in an additional vessel.

The second catalyst can be selected from among the same catalysts specified for use in stage 1 (the first catalyst), although typically the second catalyst has a greater acidity than does the first catalyst. For example, the molecular sieve component comprises ≥90 wt. % of a aluminosilicate in hydrogen form, the aluminosilicate having a constraint index in the range of from 2-12 (e.g., small crystal, H-ZSM-5). Typically, (i) the second catalyst has a silica:alumina ratio in the range of from 3 to 60, e.g., from 10 to 40, such as from 15 to 35, and (ii) the catalyst comprises <0.01 wt. % phosphorus. The form of catalyst bed can be selected from among the same bed forms utilized in reaction zone 110 or 120, e.g., one or more fixed bed, moving bed, or fluidized bed. In a particular aspect, the average temperature across any reaction zone within stage 1 (and across any catalyst bed located within a reaction zone of stage 1) is ≤700° C. Typically, the feed is not exposed to a temperature ≥700° C. at the inlet to reaction zone 110.

Second stage reaction conditions (e.g., in zone 190) generally include catalytic dehydrocyclization conditions, such as a temperature $T_2$ in the range of from 450° C. to 700° C., and a pressure $P_2 \leq 35$ psia (241.3 kPa). Typically, $T_1 \leq 0.9 \cdot T_2$, e.g., $T_1 \leq 0.85 \cdot T_2$, such as $T_1 \leq 0.8 \cdot T_2$. The pressure in stage 2 is typically less than the pressure in stage 1, e.g., $P_2 \leq 0.95 \cdot P_1$, such as $P_2 \leq 0.90 \cdot P_1$, or $P_2 \leq 0.85 \cdot P_1$, or $P_2 \leq 0.8 \cdot P_1$. Typically, reaction conditions include $T_2$ in the range of from 500° C. to 675° C. and $P_2 \leq 34$ psia (234.4 kPa), e.g., ≤32 psia (220.6 kPa), such as ≤30 psia (207 kPa), or in the range of from 10 psia (68.9 kPa) to 35 psia (241.3 kPa) or from 12 psia (82.8 kPa) to 34 psia (234.4 kPa). Generally, the reaction is carried out at a $C_{2+}$ hydrocarbon WHSV of the specified first product with respect to the second catalyst in the range of from 0.1 $hr^{-1}$ to 20 $hr^{-1}$, e.g. 0.2 $hr^{-1}$ to 5 $hr^{-1}$, or 0.3 $hr^{-1}$ to 1 $hr^{-1}$. In congruence with the first stage's WHSV, the WHSV of the second stage is based on the first product's $C_{2+}$ hydrocarbon content, and is the hourly rate of the first product's $C_{2+}$ hydrocarbon (in grams) introduced into reaction zone 190 per gram of catalyst. Those skilled in the art will appreciate that $T_1$ and $T_2$ represent average temperatures across a reaction zone, or more particularly, across a catalyst bed located within a reaction zone. Average temperature is calculated by adding the zone's inlet temperature to the zone's outlet temperature, and then dividing the sum by 2. $P_1$ and $P_2$ are not average pressures. Instead, they correspond to the inlet pressure at the specified reaction zone, e.g., reaction zone 110 for $P_1$ and reaction zone 190 for $P_2$.

Unlike stage 1, it has been found that increased reaction pressure in stage 2 (i) decreases the yield of aromatic hydrocarbon and (ii) increases the rate of catalyst coke accumulation. A stage 2 pressure of $P_2 \leq 35$ psia (241.3 kPa) is generally needed to achieve a stage 2 cycle time ≥50 hours.

Those skilled in the art will appreciate that within the ranges of process parameters specified for the second stage dehydrocyclization, there are process conditions which result in a maximum ethane conversion to aromatic hydrocarbon "$X_{ME}$". Unlike conventional multi-stage processes, the second stage typically is not operated at $X_{ME}$. Instead, process conditions are generally selected so that the initial (start of run) conversion of ethane to aromatic hydrocarbon in stage two "$X_{2E}$" is less than $X_{ME}$, e.g., $\leq 0.9 \cdot X_{ME}$. Typically, $X_{2E} \leq 0.85 \cdot X_{ME}$, e.g., $\leq 0.8 \cdot X_{ME}$, or $\leq 0.75 \cdot X_{ME}$. It has been found that operating stage two under conditions which provide $X_{2E} \geq X_{ME}$ leads to excessive catalyst coking, which typically necessitates a shortened cycle time in fixed bed operation. Since there is a net conversion of ethane in stage 2, $X_{2E}$ is greater than zero. Generally, when operating under the specified conditions using the specified feeds, $X_{2E}$ is greater than $X_{1E}$. Typically, $[1-(X_{1E}/X_{2E})]$ is ≤5, e.g., ≤2, such as ≤1, or in the range of 0.5 to 5, or 0.6 to 2, or 0.6 to 1.

Contrary to expectations, it has been found that it is detrimental to operate reaction zone 190 at a temperature sufficient for maximum conversion of the first product's ethane, typically $T_2 > 700°$ C. Doing so is observed to result in a decrease in selectivity to the desired aromatic hydrocarbon product. It also has been found that operating reaction zone 190 at a temperature >700° C. can lead to a chemical conversion of the catalyst's dehydrogenation component and a loss of catalytic dehydrocyclization activity, particularly when the dehydrogenation component comprises one or more oxide of Zn. While not wishing to be bound by any theory or model, it is believed that utilizing a temperature >700° C. results in a conversion from the oxide form to a metallic form of Zn, which has a greater vapor pressure than does the oxide form. The loss of catalytic dehydrocyclization activity is thus attributed at least partially to the evaporation of Zn from the catalyst. Typically, total ethane conversion in the second stage is ≤60%, e.g., ≤50, such as ≤40%, or in the range of from 25% to 60%, or 30% to 55%, or 30% to 50%, or 30% to 40%.

As is the case for the first stage, the second stage can include one or more additional reaction zones, e.g., a second reaction zone (not shown). The second zone of the second stage can be one that is substantially the same as reaction zone 190, namely of substantially the same bed configuration and contain substantially the same amount of substantially the same catalyst as is used in reaction zone 190. Reaction zone 190 can be operated in reaction mode while the second reaction zone is operated in regeneration mode, to regenerate the second reaction zone's catalyst. As in the first stage, continuous or semi-continuous operation can be carried out by alternating reaction and regeneration modes in the reactor 190 and the second reaction zone. Zone 190 is typically operated in dehydrocyclization mode for an average cycle time ≥50 hours, e.g., ≥75 hours, such as ≥100 hours, or ≥120 hours, at an aromatics yield that is ≥95% of that attained at the start of dehydrocyclization mode, e.g., ≥90%, such as ≥75%.

Operating stage 2 under the specified conditions with the specified catalyst typically results in converting ≥5 wt. % of the first product's ethane, e.g., ≥10 wt. %, such as ≥20 wt. %. Contrary to expectations, it has been found that appreciable conversion of the first product's ethane to aromatic hydrocarbon can be achieved with less or substantially no removal of the first product's aromatic hydrocarbon upstream of the second stage, even though $T_2$ exceeds $T_1$. Since the first product typically contains ≤5 wt. % of $C_{3+}$ hydrocarbon, e.g., ≤2 wt. % propane, and ≤1 wt. % butanes, little if any conversion of $C_{3+}$ hydrocarbon occurs in zone 190. This effect desirably decreases the accumulation of catalyst coke in stage 2.

As a result of the selective conversion of the first product's ethane, the amount of ethane (wt. %) in the second product ($A_{2P}$) is less than $A_{2F}$, and typically less than $A_{1P}$, e.g., $A_{2P} \leq 0.9 \cdot A_{1P}$, such as $A_{2P} \leq 0.75 \cdot A_{1P}$, or $A_{2P} \leq 0.5 \cdot A_{1P}$. Typically, reaction stage 2 has a greater amount of ethane conversion than reaction stage 1, e.g., $(A_{2P}/A_{2F}) \leq 0.9 \cdot (A_{1P}/A_{1P})$, such as $(A_{2P}/A_{2F}) \leq 0.75 \cdot (A_{1P}/A_{1F})$, or $(A_{2P}/A_{2F}) \leq 0.5 \cdot (A_{1P}/A_{1F})$. Typically, $A_{2F}$ is within +/−20% of $A_{2P}$, e.g., +/−10%, such as +/−5%, or +/−1%. In particular aspects, ≥95 wt. % of the first product is reacted in zone 190, $T_1 \leq 0.9 \cdot T_2$, $A_{2P} \leq 0.95 \cdot A_{1P}$ and $(A_{2P}/A_{2F}) \leq 0.95 \cdot (A_{1P}/A_{1F})$.

A second product is produced by reacting that portion of the first product entering zone 190 with the specified catalyst under the specified conditions. The second product is conducted away via line 200. Generally, the second product comprises (i) ≥0.5 wt. % of additional aromatic hydrocarbon, (ii) additional molecular hydrogen, and (iii) an amount $A_{2P}$ wt. % of ethane; wherein $A_{2P} < A_{2F}$, and $(A_{2P}/A_{2F}) < (A_{1P}/A_{1P})$. The second product generally comprises ≥1 wt.

% of total aromatic hydrocarbon, e.g., the total of (i) the additional aromatics and (ii) that portion of the first product's aromatics which are conveyed to the second stage but are not converted. Typically, the second product has a total aromatic hydrocarbon content of ≥5 wt. %, based on the weight of the second product, such as ≥10 wt. %, or in the range of from 1 wt. % to 95 wt. %, or 10 wt. % to 75 wt. %. The second product's additional aromatic hydrocarbon content is typically ≥1 wt. %, e.g., ≥2 wt. %, such as ≥10 wt. %, or ≥25 wt. %, or ≥50 wt. %, or ≥75 wt. %. The aromatic hydrocarbon produced in the second stage is "additional" in the sense that it is in addition to that produced in stage 1. The process produces a desirable BTX product. Even though $T_2$ is greater than $T_1$, it has been found that the second product has an unexpected increase in desirable xylene isomers, and an unexpected decrease yield of less desirable $C_{11+}$ aromatic hydrocarbon.

Light hydrocarbon, e.g., ethane, can be present in the second product. Methane, when present in the feed, does not typically convert to other hydrocarbon compounds under the conditions specified for stage 1 and/or stage 2; consequently when inter-stage methane separation is not used, substantially all of the feed methane typically is present in the second product. The second product will also typically include additional methane, namely that produced in stages 1 and 2, e.g., by hydrogenolysis of $C_{2+}$ hydrocarbon. The second product's methane can be recovered, and at least a portion of the recovered methane can be utilized for operating one or more of (i) fired heaters for heat transfers 112 and/or 170, (ii) electric power generation, e.g., when electric heating is used to provide at least a portion of the heat needed for sustaining the endothermic dehydrocyclization reactions of one or more of zones 110, 120, and 190, and (iii) recycle to line 100 for use as feed diluent. When ethane is present in the second product, a first portion of the second product's ethane typically is unreacted feed ethane, with a second portion typically being additional ethane produced in stage 1 and/or stage 2. At least a portion of the second product's ethane (and any other light hydrocarbon), can be recovered and recycled to line 100, for example. It has been found that the total selectivity for one or more of (i) additional methane, (ii) additional ethane, and (iii) additional $C_{3+}$ light hydrocarbon in stages 1 and 2 is unexpectedly less than would be the case if stages 1 and 2 were combined into a single stage operating under conditions specified for either stage 1 or stage 2. Typically, for a feed comprising natural gas, e.g., raw natural gas, such as Associated Gas, the process (e.g., stages 1 and 2 operating together) exhibits (i) a total conversion of $C_2$-$C_4$ hydrocarbon ≥30%, e.g., ≥40%, such as ≥50%, and (ii) a selectivity for aromatic hydrocarbon ≥30%, e.g., ≥40%, such as ≥50%. Desirably, this performance can be achieved in a single pass.

Although the catalyst used in reaction zone 190 can be substantially the same as that used in reaction zone 110 (and/or in optional reaction zone 120), typically the catalysts are different. For example, in certain aspects utilizing a feed comprising raw natural gas (<0.01 wt. % aromatic hydrocarbon), e.g., Associated Gas.

The catalyst of reaction zone 110, and of optional reaction zone 120 when used, (Catalyst A, a particular form of the first catalyst) can be present in at least one fixed bed and comprises a molecular sieve component, a dehydrogenation component, and optionally a matrix component. The molecular sieve component comprises ≥90 wt. % of a aluminosilicate in hydrogen form, the aluminosilicate having a constraint index in the range of from 2-12 (e.g., phosphorous-modified H-ZSM-5) and a silica to alumina ratio in the range of from 50 to 80. The molecular sieve component can comprise ≥95 wt. % of substantially binder free, small crystal H-ZSM-5. The dehydrogenation component comprises ≥90 wt. % of at least one oxide of Ga. The matrix component comprises ≥75 wt. % of alumina, silica, and combinations thereof. The catalyst optionally comprises ≥1 wt. % phosphorus, e.g., in the form of phosphorous-modified H-ZSM-5 and/or by including phosphorous in the matrix component.

The catalyst of reaction zone 190 (Catalyst B, a particular form of the second catalyst) also can be present in at least one fixed bed and comprises a molecular sieve component, a dehydrogenation component, and optionally a matrix component. The molecular sieve component comprises ≥90 wt. % of a aluminosilicate in hydrogen form, the aluminosilicate having a constraint index in the range of from 2-12 (e.g., small crystal H-ZSM-5) and a silica to alumina ratio in the range of from 3 to 60, e.g., from 10 to 40, such as from 15 to 35. The dehydrogenation component comprises ≥90 wt. % of at least one oxide of Zn. The matrix component when used comprises ≥90 wt. % of alumina, silica, and combinations thereof. Catalyst B typically comprises <0.01 wt. % phosphorus.

Typically, Catalyst A and Catalyst B are each located in a plurality of beds, optionally with heat added to the process at one or more locations between at least two of the fixed catalyst beds. Particularly in these aspects, the feed reacts in the presence of Catalyst A in reaction zone 110 while exposed to a temperature $T_1$ in the range of from 450° C. to 605° C. and a pressure $P_1$ in the range of from 37 psia (255.1 kPa) to 100 psia (689.5 kPa), at a space velocity (WHSV) in the range of from 0.1 hr$^{-1}$ to 20 hr$^{-1}$, such as from 0.25 hr$^{-1}$ to 2 hr$^{-1}$. Typically, the first product comprises (i) substantially the entire first product or (ii) substantially the entire first product except for that portion of the first product's molecular hydrogen which is combusted, e.g., for heat transfer 170. The first product reacts in the presence of Catalyst B in reaction zone 190 while exposed to a temperature $T_2$ in the range of from 500° C. to 675° C. and a pressure $P_2 \leq 32$ psia (220.6 kPa), at a space velocity (WHSV) in the range of from 0.1 hr$^{-1}$ to 20 hr$^{-1}$, such as from 0.25 hr$^{-1}$ to 2 hr$^{-1}$, and typically less than the WHSV used when reacting the feed in the presence of catalyst A. More particularly, $T_1 \leq 0.9 \cdot T_2$ and $P_2 \leq 0.9 \cdot P_1$, with $P_2$ in the range of 1 psia to 32 psia (220.6 kPa), e.g., 5 psia (34.5 kPa) to 30 psia (206.8 kPa), or 5 psia (34.5 kPa) to 29 psia (199.9 kPa).

It has been found that it can be beneficial for the dehydrocyclization catalyst of the first and/or second stage to have a residence time of ≤90 seconds in the dehydrocyclization reaction zone under dehydrocyclization conditions. It has been discovered that doing so dramatically increases the hyconversion of $C_{2+}$ hydrocarbon without a significant decrease in the selectivity for aromatic hydrocarbon, and without excessive selectivity for light hydrocarbon compounds such as methane. More particularly, it has been found that it is beneficial for the catalyst to have a residence time in the reaction zone under dehydrocyclization conditions of ≤60 seconds, e.g., ≤30 seconds, such as ≤seconds, or ≤1 second, or ≤0.1 second or in the range of from 0.001 second to 60 seconds. Especially when the catalyst is present in a moving bed and/or fluidized bed, it is beneficial for the catalyst to have a residence time in the dehydrocyclization reaction zone that is in the range of from 0.01 second to 10 seconds, e.g., 0.1 second to 10 seconds, such as 0.1 second to 1 second.

Solid Oxygen Carriers

Certain aspects of the invention include at least one solid oxygen carrier ("SOC"; also called an oxygen storage material) for making oxygen available for hydrogen combustion within or downstream of one or more dehydrocyclization reaction zone of the first and/or second stage. During the combustion, oxygen made available by the solid oxygen carrier reacts with the molecular hydrogen from the dehydrocyclization to produce water. SOCs are typically porous, having a pore size which is large enough to admit molecular hydrogen, but small enough to exclude the relatively large molecules, such as those of the feed and aromatic hydrocarbon product. The combustion is therefore selective for hydrogen combustion (i.e., selective hydrogen combustion, "SHC") over combustion of feed and/or product hydrocarbon. At the start of the process, the SOC is in a state conceptually identified as "$SO_xC$", indicating that oxygen is available for removal from the SOC. During dehydrocyclization, molecular hydrogen produced by that reaction enters the SOC's pores, where it combusts with the SOC's available oxygen to produce water, which can be conveniently separated from the desired aromatic hydrocarbon. Since molecular hydrogen produced in the dehydrocyclization reaction can more readily migrate into the SOC than can non-aromatic hydrocarbon feed and aromatic hydrocarbon product, equilibrium of the dehydrocyclization reaction shifts toward increased aromatic hydrocarbon production and away from hydrocarbon hydrogenation (an undesired reverse reaction that would lessen aromatic hydrocarbon yield), feed hydrocarbon oxidation, and aromatic hydrocarbon oxidation. Once the oxygen available in the SOC for combustion is depleted, the SOC will be in a reduced state conceptually identified as "$SO_{x-1}C$". The SOC can be re-oxidized from $SO_{x-1}C$ to $SO_xC$ during regeneration mode, so that the process can be repeated. The reduction and oxidation of the SOC are conceptually exemplified by the following equations:

$$H_2 + SO_xC \rightarrow H_2O + SO_{x-1}C \quad \text{(Reduction)}$$

$$O_2 + 2SO_{x-1}C \rightarrow 2SO_xC \quad \text{(Oxidation)}$$

Conventional SOCs can be used, but the invention is not limited thereto. Suitable SOCs are described in U.S. Patent Application Publication No. 2015/0065769 (where they are identified as oxygen storage materials), which is incorporated by reference herein in its entirety. One or more SOCs can be used in the aspects illustrated in FIGS. 1 and 2. For example, one or more SOCs can be used in heat transfers 112 and/or 170 in order to carry out one or more of (i) removal of molecular hydrogen from the effluent of reaction zone 110, (ii) direct heating of the effluent of reaction zone 110 by combusting, e.g., using SHC, at least a portion of the effluent's molecular hydrogen with oxygen stored with the SOC, (iii) removal of molecular hydrogen from the first product, and (iv) direct heating of the first product by combusting, e.g., using SHC, at least a portion of the first product's molecular hydrogen with oxygen stored with the SOC. After the SOC has been at least partially reduced to state $SO_{x-1}C$, it can be at least partially re-oxidized to state $SO_xC$ using oxidant. Oxidant can be obtained, e.g., from one or more of lines 140 and/or 150. To prevent oxidation of hydrocarbon in the effluent of reaction zone 110 and of hydrocarbon in the first product during re-oxidation of the SOC, valve means (not shown) can be used for isolating the SOC and for directing oxidant flow toward the SOC. Re-oxidation can be conveniently carried out when one or more dehydrocyclization reaction zones of stage 1 and/or stage 2 is operated in regeneration mode.

Since hydrogen combustion reactions including SHC produce water, dehydrocyclization catalyst proximate to or downstream of the combustion should include a dehydrogenation component that is resistant to deactivation in the presence of water. Suitable dehydrogenation components include one or more of Ga, In, Zn, Cu, Re, Mo, W, La, Fe, Ag; more particularly Ga, In, and Zn, and more particularly Ga and/or Zn.

Other aspects which include SOCs can be utilized alternatively or in addition to those described in connection with FIGS. 1 and 2. For example, one or more SOCs can be present in one or more of beds located downstream of beds of dehydrocyclization catalyst in stage 1 and/or stage 2. In other aspects, catalyst one or more beds of stage 1 and/or stage 2 contain a mixture of SOC and dehydrocyclization catalyst. In other aspects, an active material is used which includes one or more of the specified SOCs and one or more of the specified dehydrocyclization catalysts. For example, the active material can include a first component comprising SOC (optionally one having SHC functionality) and a second component comprising dehydrocyclization catalyst, e.g., as a composite. The first component can be arranged as dehydrocyclization catalyst particles in a physical mixture with a support material. Alternatively, the dehydrocyclization catalyst particles can be deposited on the support material. The second component can also be included with the physical mixture of first component and support material; alternatively in a mixture with a support material without the first component; alternatively deposited on a support material. Optionally, the second component's support material is the same as the first component's support material. The active material optionally includes additional material, such as support, binder, or matrix material.

The composite can include one or more of several forms. For example, the composite can include at least one staged composite. A "staged composite" is one in which the first component is deposited on or in a substrate downstream of the second component. Alternatively or in addition, the composite can be a layered composite, e.g., one in which the first component is arranged as a surface layer, with the second component being arranged as a sub-surface layer, or vice versa. Alternatively or in addition, the composite can include at least one monolith. Typical monoliths include ceramic structures having a plurality of substantially parallel internal passages, e.g., those in the form of a ceramic honeycomb. The first and second components can be included in the monolith, or as one or more coatings of first and/or second components on the monolith's inner surfaces, such as on the internal surfaces of one or more of the passages.

Typically, the active material's first and second components are arranged in a manner in which dehydrocyclization selectivity is optimized, with the second component being arranged relative to the first so that the SOC can make oxygen available for (i) selectively combusting molecular hydrogen produced during dehydrocyclization and (ii) providing heat for the endothermic dehydrocyclization reaction, but not so much heat as to damage the active material or cause undesired side reactions. The relative amount of first and second components in the active material is selected to achieve the specified functions. Typically, the second component, e.g., one or more SOC's, comprises greater than 10 wt. % of the active material, based on the weight of the active material. Alternatively, the second component comprises at least 20 wt. %, or at least 30 wt. %, or at least 40 wt. % of the active material.

Since adsorption is typically exothermic and desorption typically endothermic, desorption of additional oxidant (beyond that needed for SHC) may undesirably affect the process's ability to carry out the dehydrogenation reaction. Consequently, it is also desirable for the SOC to have a heat of desorption that is less than the heat needed for the dehydrogenation. For at least these reasons, SOCs comprising perovskite, material isostructural with perovskite, pyrochlore, and/or material isostructural with pyrochlore are particularly suitable, especially such of those having a pore size appropriate for selective molecular hydrogen combustion.

Regeneration Mode

Dehydrocyclization mode can be carried out in stages 1 and/or 2 for a cycle time ≥50 hours, e.g., ≥75 hours, such as ≥100 hours, or ≥120 hours, after which the process is operated in regeneration mode. It is convenient to operate both stage 1 and stage 2 in dehydrocyclization mode and then operate both stages in regeneration mode. Generally, the need for regeneration mode for a dehydrocyclization reaction zone of stages 1 and/or 2 is indicated by (i) the conversion of non-aromatic hydrocarbon in the feed (as indicated by an increase in unreacted non-aromatic hydrocarbon in the first and/or second product) is ≤90% of that at the start of dehydrocyclization mode, e.g., ≤75%, or ≤50%; and/or (ii) selectivity for aromatic hydrocarbon (indicated by the amount of aromatic hydrocarbon in the first and/or second product) is ≤90% of that at the start of dehydrocyclization mode, e.g., ≤75%, or ≤50%. Typically, when this occurs, feed flow (e.g., via line 100 of FIGS. 1 and 2) to the process is curtailed or ceased, e.g., using valve means (not shown), so that regeneration mode can be carried out. When an SOC is used during dehydrocyclization mode, the SOC will be reduced from an oxidized state (conceptually represented as $SO_xC$) to a reduced state (conceptually represented as $SO_yC$), where x and y are positive real numbers and x>y.

Regeneration mode (i) removes at least a portion of any accumulated coke and/or deposits from catalyst and reactor internals and/or (ii) stores oxygen with the SOC (in aspects where an SOC is used). Regeneration is typically carried out at a temperature ≤700° C. Exceeding this temperature during regeneration has been found to result in de-alumination and/or loss of structure of the dehydrocyclization catalyst, leading to an undesirable loss of catalyst acidity. Regeneration is typically carried out using procedures which limit the maximum temperature to which a dehydrocyclization catalyst is exposed to about 750° C., more typically to about 650° C. Typically, regeneration mode is carried out for a time duration ≤24 hours, e.g., ≤12 hours. Conventional regeneration methods can be used, e.g., introducing oxidant, such as air or oxygen in air, into the reaction zone operating in regeneration mode for a time sufficient to remove at least a portion of any accumulated coke, but the invention is not limited thereto. When stages 1 and/or 2 are carried out in a set of fixed-bed, adiabatic reactors in series, a suitable regeneration procedure includes circulating a stream of regeneration gas containing a limited amounts of oxidant (typically oxygen), which limits the size of the exotherm where coke is burned off the dehydrocyclization catalyst. Typically, at the location where the regeneration gas enters the first (most upstream, with respect to the flow of regeneration gas) reactor, e.g., at the reactor's inlet, the regeneration gas is exposed to a temperature ≤350° C., e.g., ≤325° C., such as ≤300° C. If needed, the oxidant content of the regenerating gas can be decreased to lessen the risk of exceeding the maximum temperature. In aspects illustrated in FIGS. 1 and 2, regeneration gas can be obtained from the same source as that used for oxidant of lines 140 and/or 150.

In aspects using one or more SOCs, regeneration mode typically includes replenishing at least a portion of the SOC's oxidant that was consumed during dehydrocyclization mode and removing at least a portion of the dehydrocyclization catalyst's (or active material's) accumulated coke. The SOC is oxidized (or re-oxidized) during regeneration mode from state $SO_yC$ to state $SO_zC$, where z is a positive real number and z>y. Once oxidized to state $SO_zC$, the SOC can again function as a source of oxidant for the selective molecular hydrogen combustion reaction, which is also carried out in the reaction zone. Although z can have substantially the same value as x, this is not required.

In an alternative aspect, replenishment of the SOC's depleted oxygen is not carried out. In such cases, spent active material or the SOC component thereof is removed from the reaction zone and replaced with fresh or regenerated material having sufficient oxidant content for the dehydrogenation/combustion. Replacement can be carried out continuously, e.g., utilizing conventional fluidized catalyst or slurry catalyst technology, in a batch method, and in combinations thereof.

All patents, test procedures, and other documents cited herein, including priority documents, are fully incorporated by reference to the extent such disclosure is not inconsistent and for all jurisdictions in which such incorporation is permitted. Although certain aspects are described herein with particularity, other aspects will be apparent to and can be readily practiced by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa.

The invention claimed is:
1. A hydrocarbon conversion process, comprising:
(a) providing a feed comprising ≥1 wt. % of non-aromatic hydrocarbon,
(b) providing first and second catalysts, wherein (i) the first catalyst comprises ≥10 wt. % of a first molecular sieve component and ≥0.005 wt. % of a first dehydrogenation component and (ii) the second catalyst comprises ≥10 wt. % of a second molecular sieve component and ≥0.005 wt. % of a second dehydrogenation component;
(c) contacting the feed with the first catalyst under catalytic dehydrocyclization conditions including a temperature $T_1$ in the range of from 400° C. to 630° C. to produce a first product comprising ≥1 wt. % aromatic hydrocarbon; and
(d) contacting ≥50 wt. % of the first product, including ≥50 wt. % of the first product's aromatic hydrocarbon, with the second catalyst under catalytic dehydrocyclization conditions including a temperature $T_2$ in the range of from 450° C. to 700° C., to produce a second product comprising ≥1 wt. % of additional aromatic hydrocarbon, wherein $T_1 \leq 0.9 \cdot T_2$.

2. The process of claim 1, wherein (i) the first and second molecular sieve components each comprise (i) one or more of MCM-22, ZSM-5, ZSM-11, ZSM-12, ZSM-22, ZSM-23, ZSM-35, and ZSM-48 and/or (ii) the first and second dehydrogenation components each comprise one or more of Ga, Zn, Cu, Re, Mo, W, La, Fe, Ag, Pt, and Pd.

3. The process of claim 1, wherein the first and second catalysts have substantially the same composition.

4. The process of claim 1, wherein
(i) the catalytic dehydrocyclization conditions of step (c) include one or more of $T_1$ in the range of from 450° C. to 605° C., an ethane conversion $X_{1E}$, a pressure $P_1$ in the range of from 37 psia (255.1 kPa) to 80 psia (522 kPa), and a space velocity (WHSV) in the range of from 0.1 hr$^{-1}$ to 20 hr$^{-1}$;
(ii) the catalytic dehydrocyclization conditions of step (d) include one or more of $T_2$ in the range of from 500° C. to 675° C., an ethane conversion $X_{2E}$, a pressure $P_2 \leq 30$ psia (207 kPa), and a space velocity (WHSV) in the range of from 0.1 hr$^{-1}$ to 20 hr$^{-1}$; and
(iii) $[1-(X_{1E}/X_{2E})] \leq 2$.

5. The process of claim 1, wherein
(i) the feed comprises ≥50 wt. % of non-aromatic hydrocarbon, the non-aromatic hydrocarbon comprising methane, 10 wt. % to 40 wt. % ethane, propane, and butanes;
(ii) the first product further comprises ≥90 wt. % of the feed's ethane;
(iii) the first product further comprises additional paraffinic hydrocarbon including additional methane and additional ethane;
(iv) the additional aromatic hydrocarbon includes aromatic hydrocarbon produced during step (d) by converting at least 10 wt. % of the first product's total ethane; and
(v) no more than 10 wt. % of the feed's ethane is converted during step (c).

6. The process of claim 1, wherein
(i) the feed comprises ≥75 wt. % of non-aromatic hydrocarbon, the non-aromatic hydrocarbon comprising 1 wt. % to 40 wt. % methane, 10 wt. % to 40 wt. % ethane, 20 wt. % to 50 wt. % propane, 20 wt. % to 50 wt. % butanes, and substantially saturated $C_{5+}$ hydrocarbon;
(ii) the first product comprises ≥10 wt. % of unconverted feed ethane, ≥10 wt. % of unconverted feed methane, ≥5 wt. % aromatic hydrocarbon, ≤2 wt. % propane, and ≤1 wt. % butanes;
(iii) step (d) includes contacting with the second catalyst ≥90 wt. % of the first product, including ≥90 wt. % of the first product's aromatic hydrocarbon; and
(iv) the second product comprises ≥5 wt. % of additional aromatic hydrocarbon.

7. The process of claim 1, further comprising selectively oxidizing molecular hydrogen during one or more of (i) step (c), (ii) after step (c) but before step (d), and (iii) step (d).

8. The process of claim 7, wherein the selective oxidation includes contacting hydrogen with oxygen released from at least one solid oxygen carrier (SOC).

9. The process of claim 8, wherein the SOC includes perovskite and the first and/or second catalyst is composited with at least a portion of the SOC.

10. The process of claim 8, further comprising (i) regenerating the first and/or second catalyst and (ii) adding oxygen to the SOC.

11. A hydrocarbon upgrading process, comprising:
(a) providing a feed comprising $A_{1F}$ wt. % ethane, $A_{1F}$ being at least 10; 1 wt. % to 40 wt. % methane; 20 wt. % to 50 wt. % propane; and 20 to 50 wt. % butanes;
(b) providing first and second catalysts, wherein (i) the first catalyst comprises ≥25 wt. % of a first molecular sieve component and ≥0.5 wt. % of a first dehydrogenation component and (ii) the second catalyst comprises ≥25 wt. % of a second molecular sieve component and ≥0.5 wt. % of a second dehydrogenation component;
(c) contacting the feed with the first catalyst under catalytic dehydrocyclization conditions including a temperature $T_1$ in the range of from 400° C. to 630° C., an ethane conversion $X_{1E}$, and a pressure $P_1$ to produce a first product comprising ≥10 wt. % aromatic hydrocarbon; $A_{1P}$ wt. % ethane, $A_{1P}$ being greater than or equal to $A_{1E}$; 1 wt. % to 40 wt. % methane, ≤1 wt. % propane, and ≤1 wt. % butanes; and
(d) contacting with the second catalyst ≥50 wt. % of the first product, including ≥50 wt. % of the first product's aromatic hydrocarbon and ≥50 wt. % of the first product's ethane, under catalytic dehydrocyclization conditions including a temperature $T_2$ in the range of from 450° C. to 700° C., an ethane conversion $X_{2E}$, and a pressure $P_2$ that does not exceed 35 psia (241.3 kPa) to produce a second product comprising at least 0.5 wt. % of additional aromatic hydrocarbon and an amount $A_{2P}$ wt. % of ethane; wherein $T_1$ does not exceed $0.9 \cdot T_2$, $P_2$ is less than $P_1$, $X_{1E}$ is less than $X_{2E}$, and $A_{2P}$ does not exceed $0.95 \cdot A_{1P}$.

12. The process of claim 11, wherein (i) the first catalyst comprises at least 90 wt. % of the first molecular sieve component; the second catalyst comprises at least 90 wt. % of the second molecular sieve component; the first and second molecular sieve components each comprise one or more of MCM-22, ZSM-5, ZSM-11, ZSM-12, ZSM-22, ZSM-23, ZSM-35, and ZSM-48; the first catalyst comprises at least 1 wt. % the first dehydrogenation component; the second catalyst comprises at least 1 wt. % the second dehydrogenation component; and the first and second dehydrogenation components each comprise two or more of Ga, Zn, Cu, Re, Mo, W, La, Fe, Ag, Pt, and Pd.

13. The process of claim 11, wherein
(i) the first catalyst comprises at least 50 wt. % of the first molecular sieve component and at least 1 wt. % of the first dehydrogenation component;
(ii) the first molecular sieve component comprises at least 90 wt. % of (A) ZSM-5 and/or (B) ZSM-12; and
(iii) The first dehydrogenation component comprises ≥90 wt. % of (A) Ga and/or (B) Zn.

14. The process of claim 11, wherein
(i) the catalytic dehydrocyclization conditions of step (c) include one or more of include one or more of $T_1$ in the range of from 450° C. to 605° C., $P_1$ in the range of from 37 psia (255.1 kPa) to 80 psia (522 kPa), and a weight hourly space velocity (WHSV) in the range of from 0.1 hr$^{-1}$ to 20 hr$^{-1}$;
(ii) the catalytic dehydrocyclization conditions of step (d) include one or more of $T_2$ in the range of from 500° C. to 675° C., $P_2 \leq 30$ psia (207 kPa), and a space velocity (WHSV) in the range of from 0.1 hr$^{-1}$ to 20 hr$^{-1}$;
(iii) the first dehydrogenation component comprises at least 95 wt. % Ga;

(iv) the first molecular sieve component comprises at least 90 wt. % of aluminosilicate having a silica:alumina ratio in the range of from 50 to 80;
(v) the second dehydrogenation component comprises at least 95 wt. % Zn; and
(vi) the second molecular sieve component comprises at least 90 wt. % of aluminosilicate having a silica:alumina ratio in the range of from 10 to 40.

15. The process of claim 11, wherein
(i) the feed is derived from unfractionated natural gas;
(ii) $A_{1F}$ is at least 20 wt. %, and the first product comprises at least 25 wt. % aromatic hydrocarbon, at least 2 wt. % molecular hydrogen, at least 10 wt. % methane, no more than 2 wt. % propane, and no more than 1 wt. % butanes;
(iii) step (d) includes contacting with the second catalyst ≥95 wt. % of the first product, including ≥95 wt. % of the first product's aromatic hydrocarbon and ≥95 wt. % of the first product's ethane;
(iv) $A_{2P}$ does not exceed $0.75 \cdot A_{1P}$, $[1-(X_{1E}/X_{2E})] \leq 2$, and the second product comprises at least 1 wt. % of the additional aromatic hydrocarbon;
(v) $P_2$ does not exceed $0.8 \cdot P_1$; and
(vi) step (d) is carried out for an average cycle time ≥120 hours.

16. The process of claim 11, further comprising producing a raffinate by removing from the second product an extract comprising ≥90 wt. % of any of the aromatic hydrocarbon in the second product and at least 90 wt. % of the additional aromatic hydrocarbon, wherein
(i) the raffinate comprises no more than 12 wt. % ethane, no more than 5 wt. % propane, no more than 2 wt. % butanes, and at least 95 wt. % the balance of the raffinate comprises methane;
(ii) the raffinate has a Wobbe Index in the range of from 49.01 MJ/sm³ to 52.22 MJ/sm³ and has heating value in the range of from 36.07 MJ/sm³ to 41.40 MJ/sm³, and
(iii) the process does not include cryogenic methane separation before step (a).

17. The process of claim 11, further comprising oxidizing molecular hydrogen during one or more of (i) step (c), (ii) after step (c) but before step (d), and (iii) step (d).

18. The process of claim 17, wherein the oxidation is selective hydrogen combustion, and includes contacting hydrogen with oxygen released from at least one solid oxygen carrier (SOC).

19. The process of claim 18, wherein the SOC includes perovskite and the first and/or second catalyst is composited with at least a portion of the SOC.

20. The process of claim 18, further comprising (i) regenerating the first and/or second catalyst and (ii) adding oxygen to the SOC.

21. A process for upgrading paraffinic hydrocarbon, comprising:
(a) providing a feed comprising $A_{1F}$ wt. % ethane, $A_{1F}$ being less than 1; no more than 1 wt. % of aromatic hydrocarbon; and at least 1 wt. % of $C_{3+}$ paraffinic hydrocarbon;
(b) providing first and second catalysts, wherein (i) the first catalyst comprises at least 25 wt. % of a first molecular sieve component and at least 0.5 wt. % of a first dehydrogenation component and (ii) the second catalyst comprises at least 25 wt. % of a second molecular sieve component and at least 0.5 wt. % of a second dehydrogenation component;
(c) contacting the feed with the first catalyst under catalytic dehydrocyclization conditions including a temperature $T_1$ in the range of from 400° C. to 630° C. and a pressure $P_1$, to produce a first product comprising at least 10 wt. % aromatic hydrocarbon; an amount $A_{1P}$ wt. % of ethane, $A_{1P}$ being at least 1; 1 wt. % to 40 wt. % methane; no more than 2 wt. % propane; and no more than 1 wt. % butanes; and
(d) contacting ≥50 wt. % of the first product, including ≥50 wt. % of the first product's aromatic hydrocarbon and ≥50 wt. % of the first product's ethane, with the second catalyst under catalytic dehydrocyclization conditions, including a temperature $T_2$ in the range of from 450° C. to 700° C., and a pressure $P_2$ that does not exceed 35 psia (241.3 kPa), to produce a second product comprising at least 1 wt. % of additional aromatic hydrocarbon and an amount $A_{2P}$ wt. % of ethane; wherein $T_1$ does not exceed $0.9 \cdot T_2$, $P_2$ is less than $P_1$, and $A_{2P}$ does not exceed $0.95 \cdot A_{1P}$.

22. The process of claim 21, wherein
(i) the catalytic dehydrocyclization conditions of step (c) include one or more of $T_1$ in the range of from 450° C. to 605° C., $P_1$ in the range of from 37 psia (255.1 kPa) to 80 psia (522 kPa), and a space velocity (WHSV) in the range of from 0.1 hr⁻¹ to 20 hr⁻¹, and
(ii) the catalytic dehydrocyclization conditions of step (d) include one or more of $T_2$ in the range of from 500° C. to 675° C., $P_2 \leq 30$ psia (207 kPa), and a space velocity (WHSV) in the range of from 0.1 hr⁻¹ to 20 hr⁻¹.

23. The process of claim 21, wherein
(i) $A_{1F}$ does not exceed 0.1 and $A_{1P} \geq 10$;
(ii) the first product comprises at least 25 wt. % aromatic hydrocarbon, and 10 wt. % to 40 wt. % methane;
(iii) step (c) includes contacting the second catalyst with ≥90 wt. % of the first product, including ≥90 wt. % of the first product's aromatic hydrocarbon, ≥90 wt. % of the first product's ethane, and ≥90 wt. % of the first product's methane;
(iv) $A_{2P}$ does not exceed $0.75 \cdot A_{1P}$, and the second product comprises at least 2 wt. % of the additional aromatic hydrocarbon; and
(v) step (c) has a total ethane conversion $X_{1E}$, step (d) has a total ethane conversion $X_{2E}$, and $[1-(X_{1E}/X_{2E})] \leq 2$.

24. The process of claim 21, wherein
(i) the first dehydrogenation component comprises at least 95 wt. % Ga;
(ii) the first molecular sieve component comprises at least 95 wt. % of small crystal, substantially binder free H-ZSM-5 and further comprises at least 1 wt. % phosphorous, and has a silica:alumina ratio in the range of from 50 to 80;
(iii) the second dehydrogenation component comprises at least 95 wt. % Zn;
(iv) the second molecular sieve component comprises at least 95 wt. % of small crystal H-ZSM-5 and has a silica:alumina ratio in the range of from 10 to 40; and
(v) the first catalyst comprises no more than 1 wt. % of matrix.

25. A natural gas upgrading process, comprising:
(a) providing a natural gas feed comprising methane and $A_{1F}$ wt. % ethane wherein $A_{1F}$ is ≥13;
(b) providing first and second catalysts, wherein (i) the first catalyst comprises ≥25 wt. % of a first molecular sieve component and ≥0.5 wt. % of a first dehydrogenation component and (ii) the second catalyst comprises ≥25 wt. % of a second molecular sieve component and ≥0.5 wt. % of a second dehydrogenation component;

(c) contacting the feed with the first catalyst under catalytic dehydrocyclization conditions, including a temperature $T_1$ in the range of from 400° C. to 630° C., a pressure $P_1$, and an ethane conversion $X_{1E}$, to produce a first product comprising ≥10 wt. % aromatic hydrocarbon; $A_{1P}$ wt. % ethane, wherein $A_{1P} \geq A_{1F}$; methane; no more than 2 wt. % propane; and no more than 1 wt. % butanes;

(d) contacting with the second catalyst ≥50 wt. % of the first product, including ≥50 wt. % of the first product's aromatic hydrocarbon, ≥50 wt. % of the first product's ethane, and ≥50 wt. % of the first product's methane, the contacting being carried out under catalytic dehydrocyclization conditions which include a temperature $T_2$ in the range of from 450° C. to 700° C., a pressure $P_2$ that does not exceed 35 psia (241.3 kPa), and an ethane conversion $X_{2E}$ to produce a second product comprising ≥2 wt. % of additional aromatic hydrocarbon and $A_{2P}$ wt. % of ethane; wherein:

(i) $T_1$ does not exceed $0.9 \cdot T_2$,
(ii) $P_2$ does not exceed $0.9 \cdot P_1$,
(iii) $A_{2P}$ does not exceed $0.95 \cdot A_{1P}$,
(iv) $[1-(X_{1E}/X_{2E})] \leq 2$, and (e) producing a raffinate by removing from the second product an extract comprising ≥90 wt. % of the first product's aromatic hydrocarbon that is present in the second product and ≥90 wt. % of the additional aromatic hydrocarbon, wherein (i) the raffinate comprises no more than 12 wt. % ethane, no more than 5 wt. % propane, and no more than 2 wt. % butanes, with at least 95 wt. % the balance of the raffinate comprises methane,
(ii) the raffinate has a Wobbe Index in the range of from 49.01 MJ/sm$^3$ to 52.22 MJ/sm$^3$ and has heating value in the range of from 36.07 MJ/sm$^3$ to 41.40 MJ/sm$^3$, and
(iii) the process does not include cryogenic methane separation.

* * * * *